United States Patent

Osadchy et al.

[11] Patent Number: 6,147,480
[45] Date of Patent: Nov. 14, 2000

[54] DETECTION OF METAL DISTURBANCE

[75] Inventors: Daniel Osadchy, Haifa; Assaf Govari, Kiriat Haim, both of Israel

[73] Assignee: Biosense, Inc., New Brunswick, N.J.

[21] Appl. No.: 09/173,763

[22] Filed: Oct. 15, 1998

Related U.S. Application Data

[60] Provisional application No. 60/063,009, Oct. 23, 1997.

[51] Int. Cl.[7] ............................ G01R 19/00; G01S 5/04; G01S 3/02; H01F 30/12
[52] U.S. Cl. ........................ 324/67; 342/442; 342/448; 342/459; 336/5; 607/122
[58] Field of Search ............................ 324/67; 342/442, 342/448, 459; 607/122, 123, 124, 125, 126, 127, 128; 336/5

[56] References Cited

U.S. PATENT DOCUMENTS

| | | | |
|---|---|---|---|
| 3,644,825 | 2/1972 | Davis, Jr. et al. | 324/41 |
| 3,868,565 | 2/1975 | Kuipers | 324/34 R |
| 4,017,858 | 4/1977 | Kuipers | 343/100 R |
| 4,054,881 | 10/1977 | Raab | 343/112 R |
| 4,287,809 | 9/1981 | Egli et al. | 89/41.21 |
| 4,317,078 | 2/1982 | Weed et al. | 324/208 |
| 4,416,289 | 11/1983 | Bresler . | |
| 4,526,177 | 7/1985 | Rudy et al. . | |
| 4,560,930 | 12/1985 | Kouno | 324/207 |
| 4,613,866 | 9/1986 | Blood | 343/448 |
| 4,642,786 | 2/1987 | Hansen | 364/559 |
| 4,651,436 | 3/1987 | Gaal | 33/533 |
| 4,710,708 | 12/1987 | Rorden et al. | 324/207 |
| 4,849,692 | 7/1989 | Blood | 324/208 |
| 4,905,698 | 3/1990 | Strohl, Jr. et al. | 128/653 R |
| 4,945,305 | 7/1990 | Blood | 324/207.17 |
| 5,002,137 | 3/1991 | Dickinson et al. | 175/19 |
| 5,042,486 | 8/1991 | Pfeiler et al. | 128/653 R |
| 5,068,608 | 11/1991 | Clark, Jr. | 324/220 |
| 5,099,845 | 3/1992 | Besz et al. | 128/653.1 |
| 5,172,056 | 12/1992 | Voisin | 324/207.17 |
| 5,211,165 | 5/1993 | Dumoulin et al. | 128/653.1 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,265,610 | 11/1993 | Darrow et al. | 128/653.1 |
| 5,269,289 | 12/1993 | Takehana et al. | 128/4 |
| 5,273,025 | 12/1993 | Sakiyama et al. | 128/6 |
| 5,309,913 | 5/1994 | Kormos et al. | 128/653.1 |
| 5,325,873 | 7/1994 | Hirschi et al. | 128/899 |
| 5,375,596 | 12/1994 | Twiss et al. | 128/653.1 |
| 5,377,678 | 1/1995 | Dumoulin et al. | 128/653.1 |
| 5,425,367 | 6/1995 | Shapiro et al. | 128/653.1 |
| 5,425,382 | 6/1995 | Golden et al. | 128/899 |
| 5,429,132 | 7/1995 | Guy et al. | 128/653.1 |
| 5,437,277 | 8/1995 | Dumoulin et al. | 128/653.1 |

(List continued on next page.)

FOREIGN PATENT DOCUMENTS

| | | | |
|---|---|---|---|
| WO 92/03090 | 3/1992 | WIPO | A61B 5/06 |
| WO 94/04938 | 3/1994 | WIPO | G01S 3/14 |
| WO 94/23647 | 10/1994 | WIPO | A61B 5/05 |
| WO 96/05768 | 2/1996 | WIPO | A61B 5/06 |
| WO 96/41119 | 12/1996 | WIPO | G01B 7/14 |
| WO 97/29678 | 8/1997 | WIPO . | |
| WO 97/29679 | 8/1997 | WIPO . | |
| WO 97/29709 | 8/1997 | WIPO | A61B 19/00 |
| WO 97/29710 | 8/1997 | WIPO | A61B 19/00 |
| WO 97/32179 | 9/1997 | WIPO | G01B 7/14 |
| WO 97/42517 | 11/1997 | WIPO . | |

*Primary Examiner*—Thomas H. Tarcza
*Assistant Examiner*—Fred H. Mull
*Attorney, Agent, or Firm*—Louis J. Capezzuto

[57] ABSTRACT

A method for tracking an object using energy fields, in the presence of interference due to introduction of an article responsive to the fields, in the vicinity of the object. One or more desired energy fields are produced in the vicinity of the object, and a characteristic of energy fields induced due to introduction of the article is determined. Signals are generated responsive to the energy fields at a plurality of locations of the object after introduction of the article. Spatial coordinates of the object are determined, responsive to the generated signals and the determined characteristic.

19 Claims, 3 Drawing Sheets

U.S. PATENT DOCUMENTS

| | | | |
|---|---|---|---|
| 5,443,489 | 8/1995 | Ben-Haim | 607/115 |
| 5,453,687 | 9/1995 | Zierdt et al. | 324/207.17 |
| 5,558,091 | 9/1996 | Acker et al. | 128/653.1 |
| 5,577,502 | 11/1996 | Darrow et al. | 128/653.1 |
| 5,622,169 | 4/1997 | Golden et al. | 128/653.1 |
| 5,682,886 | 11/1997 | Delp et al. | 128/653.1 |
| 5,694,945 | 12/1997 | Ben-Haim | 128/736 |
| 5,715,822 | 2/1998 | Watkins et al. | 128/653.5 |
| 5,729,129 | 3/1998 | Acker et al. | 324/207.12 |
| 5,752,513 | 5/1998 | Acker et al. | 128/653.1 |
| 5,769,843 | 6/1998 | Abela et al. | 606/10 |

DETECTION OF METAL DISTURBANCE

This application is a nonprovisional patent application of provisional patent application: U.S. Ser. No. 60/063,009 filing Oct. 23, 1997.

FIELD OF THE INVENTION

The present invention relates generally to apparatus for generating and detecting electromagnetic fields, and specifically to non-contact, electromagnetic methods and devices for tracking the position and orientation of an object.

BACKGROUND OF THE INVENTION

Non-contact electromagnetic tracking systems are well known in the art, with a wide range of applications.

For example, U.S. Pat. No. 4,054,881 describes a tracking system using three coils to generate electromagnetic fields in the vicinity of an object being tracked. The fields generated by these three coils are distinguished from one another by open loop multiplexing of time, frequency or phase. The signal currents flowing in three orthogonal sensor coils are used to determine the object's position, based on an iterative method of computation.

U.S. Pat. No. 5,391,199, filed Jul. 20, 1993, which is assigned to the assignee of the present application and whose disclosure is incorporated herein by reference, describes a system for generating three-dimensional location information regarding a medical probe or catheter. A sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT patent publication WO/96/05768, filed Jan. 24, 1995, which is assigned to the assignee of the present application and whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates. As in the case of the '539 patent application described above, the radiator coils preferably operate simultaneously at different frequencies, for example at 1000, 2000 and 3000 Hz, respectively.

The above tracking systems rely on separation of position-responsive signals into components, most typically frequency components, wherein each such component is assumed to correspond uniquely to a single radiator coil, in a known position, radiating a magnetic field having a regular, well-defined spatial distribution. In practice, however, when a metal or other magnetically-responsive article is brought into the vicinity of the catheter or other object being tracked, the magnetic fields generated in this vicinity by the radiator coils are distorted. For example, the radiator coil's magnetic field may generate eddy currents in such an article, and the eddy currents will then cause a parasitic magnetic field to be radiated. Such parasitic fields and other types of distortion can lead to errors in determining the position of the object being tracked.

SUMMARY OF THE INVENTION

It is an object of some aspects of the present invention to provide a method for improving the accuracy of position determination by a non-contact object tracking system.

In one aspect of the present invention, the position determination is corrected so as to account for disturbances of an energy field used in tracking the object due to metal or other field-responsive articles in the vicinity of the object being tracked.

In another aspect of the present invention, such disturbances are detected, so as to alert a user of the system that the accuracy of position determination may be compromised.

In preferred embodiments of the present invention, the energy field comprises a magnetic field, which causes position-responsive electrical signals to be generated in one or more coils associated with the object being tracked, for example a catheter or other medical probe.

The present invention relies on the fact that parasitic magnetic fields, generated by metal or other field-responsive articles that receive and re-radiate energy from a radiator coil magnetic field are typically at the same frequency as the radiator coil field, but are shifted in phase relative thereto. The phase shift and the amplitudes of the parasitic fields generally depend on properties of the article, including dielectric constant, magnetic permeability and geometrical shape. Furthermore, when the article introduced into the magnet field is substantially magnetizable, i.e., its permeability is significantly different from the permeability of air, the lines of magnetic field in the vicinity of the article are generally distorted. Distortion of this type does not, however, substantially affect the phase of the magnetic field.

In preferred embodiments of the present invention, an object tracking system comprises one or more sensor coils adjacent to a locatable point on an object being tracked, and one or more radiator coils, which generate magnetic fields when driven by electrical currents at respective driving frequencies in a vicinity of the object. Preferably each of the radiator coils has its own frequency, which is different from the frequencies of all the other radiator coils. Alternatively, however, two or more of the radiator coils may share a common frequency, and may be time-multiplexed so that only one of the two or more coils is driven to generate a magnetic field at any given time.

The sensor coils generate electrical signals responsive to the magnetic fields, which signals are received by signal processing circuitry and analyzed by a computer or other processor. When a metal or other field-responsive article is in the vicinity of the object, the signals typically include position signal components responsive to the magnetic fields generated by the radiator coils at their respective driving frequencies, and parasitic signal components responsive to parasitic magnetic fields generated due to the article. The computer processes the signals to identify the parasitic components, preferably using a phase-sensitive method, as described below, and uses the position signal components to determine the position of the object.

In some such preferred embodiments of the present invention, the signals due to the magnetic field generated by each of the radiator coils are first detected in the absence of any articles that could cause parasitic signal components to be generated. Baseline phases of the signals at each of the radiator coil frequencies, which are substantially independent of the position of the object relative to the radiator coils, are then determined relative to the phase of the current driving the respective radiator coil. When an article that generates parasitic magnetic fields is introduced into the vicinity of the object, at least some signal components generated by the sensor coils in response to the parasitic fields will generally be shifted in phase relative to the pre-determined baseline phase. The phase shift of the signals due to the parasitic signal components is detected and may be used to indicate that the position of the object determined by the computer may be inaccurate due to the presence of the article in the object's vicinity.

Additionally or alternatively, while a metal or other field-responsive article is being moved into the vicinity of the object being tracked, the object is preferably held still. Changes in the amplitude and phase of the signals received from the sensor coils are then known to be associated with distortions of the magnetic field due to the article. These changes are detected and used in assessing the effect of the distortions on the determination of the object's position coordinates.

In particular, the detected changes may be used to measure the phase shifts of the parasitic fields, relative to the radiator coil fields. In some cases, these phase shifts will be generally constant, independent of the position and orientation of the field-responsive article, for example, if the article is substantially symmetrical. Similarly, if the article comprises highly-conductive material, having negligible resistivity, the phase shift of the parasitic fields will be close to 90°, generally independent of the position and orientation of the article. Although not all articles will have such generally constant phase shifts, the dependence of the phase shift on position and orientation can be determined empirically in each case.

In other preferred embodiments of the present invention, a characteristic of the article, such as the distortion of the magnetic field that the article induces or the effect of the article on the determination of the object's coordinates, is known, for example based on prior measurement. The known characteristic may be used to correct the determination of the coordinates, as described below.

In some preferred embodiments of the present invention, the signals generated by the sensor coils are detected using a harmonic detection method, more preferably with the detection frequency synchronized with the frequencies of the radiator coils. Signal components that are out of phase with the baseline phase are eliminated from the sampled signal, for example using phase-sensitive signal correlation or other methods known in the art, thereby substantially removing at least some of the parasitic signal components and improving the accuracy of position determination in the presence of the metal or other field-responsive article.

Preferably, if the phase shifts of the parasitic fields are known, having been measured as described above, for example, then the known phase shifts may be used in analyzing the signals so as to remove at least a portion of the parasitic signal components therefrom.

There is therefore provided, in accordance with a preferred embodiment of the present invention, a method for tracking an object using an energy field, in the presence of interference due to introduction of an article responsive to the field, in the vicinity of the object, including:

producing a first energy field in the vicinity of the object;

determining a characteristic of a second energy field induced responsive to the first field, due to introduction of the article;

receiving signals responsive to the first and second energy fields generated at a plurality of locations of the object after introduction of the article; and determining spatial coordinates of the object responsive to the generated signals and the determined characteristic.

Preferably, determining the characteristic includes determining a phase shift of the signals responsive to the second energy field with respect to the signals responsive to the first energy field. Preferably, the characteristic is not determined from measurements made at the location.

In a preferred embodiment of the invention, determining spatial coordinates includes determining an amplitude of the signals generated at a location of the object; processing the amplitude to find a corrected amplitude, using the determined characteristic; and calculating the coordinates based on the corrected amplitude.

Preferably, determining the characteristic of the induced energy fields includes receiving a first signal responsive to the energy field in the absence of the field-responsive article; introducing the article into the vicinity of the object; receiving a second signal responsive to the energy field in the presence of the article; and processing the first and second signals to determine the characteristic.

Preferably, processing the first and second signals includes finding a first amplitude and a first phase of the first signal; finding a second amplitude and a second phase of the second signal; and determining a phase shift associated with the induced field, based on the first and second amplitudes and the first and second phases.

In a preferred embodiment of the invention, determining spatial coordinates includes measuring an uncorrected amplitude and an uncorrected phase of the signals received at one of the plurality of locations of the object; finding a corrected amplitude, using the phase shift associated with the induced field; and calculating the coordinates based on the corrected amplitude.

In another preferred embodiment, the method includes detecting a malfunction in a system for tracking the object by finding a variability in one or more of the first and second phases.

In still another preferred embodiment, the method includes detecting the second energy field and notifying a user that the article has been introduced.

Additionally or alternatively, determining the spatial coordinates of the object includes estimating an error bound on the coordinates in the presence of the article.

Preferably, producing the energy fields includes producing magnetic fields, and receiving the signals includes receiving electrical signals which are generated responsive to the magnetic field.

There is further provided, in accordance with a preferred embodiment of the present invention, an object tracking system, including:

a radiator, which generates an energy field in the vicinity of the object;

a sensor, fixed to the object, which generates signals responsive to the energy field; and signal processing circuitry, which receives the signals from the sensor and determines position coordinates of the object responsive thereto, while detecting interference in the signals due to introduction into the vicinity of the object of an article responsive to the energy field.

Preferably, the circuitry detects a phase shift in the signals due to the introduction of the article. Further preferably, based on the detected phase shift, the circuitry corrects the position coordinates for errors induced due to the interference.

In a preferred embodiment of the invention, the circuitry detects a malfunction in the system by finding a variability in the phase shift.

In another preferred embodiment, the circuitry notifies a user of the system that the article has been introduced, based on the detected interference.

Additionally or alternatively, the circuitry determines an error bound on the coordinates, based on the detected interference.

Preferably, the energy field includes a magnetic field, and the signals include electrical currents generated responsive to the magnetic field.

BRIEF DESCRIPTION OF THE DRAWINGS

The present invention will be more fully understood from the following detailed description of the preferred embodiments thereof, taken together with the drawing in which.

DETAILED DESCRIPTION OF PREFERRED EMBODIMENTS

Figure 1:
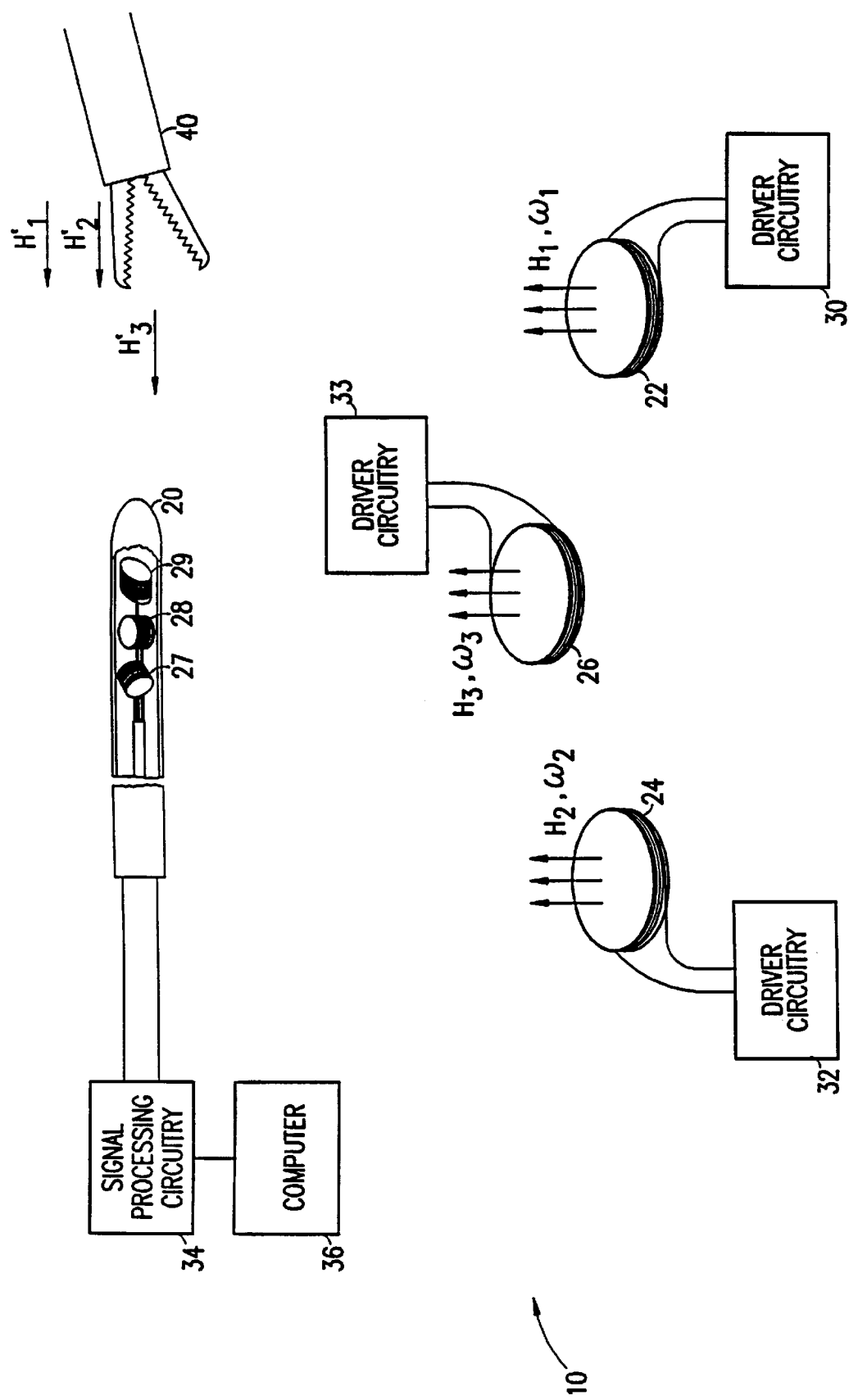
FIG. 1 is a schematic representation of an object tracking system operative in accordance with a preferred embodiment of the present invention.

Reference is now made to FIG. 1, which schematically illustrates a system 10 for tracking a probe 20, such as a catheter for medical use, in accordance with preferred embodiment of the present invention. As described in the above-referenced U.S. Pat. No. 5,391,199 and PCT patent publication WO/96/05768, system 10 comprises a plurality of radiator coils 22, 24 and 26. These coils generate respective magnetic fields $\vec{H}_1$, $\vec{H}_2$ and $\vec{H}_3$, at respective frequencies $\omega_1$, $\omega_2$ and $\omega_3$, in the vicinity of probe 20. The probe includes sensor coils 27, 28 and 29, which generate electrical current signals in response to the magnetic fields. These signals comprise components at frequencies $\omega_1$, $\omega_2$ and $\omega_3$, whose respective amplitudes are dependent on the position and orientation of probe 20.

System 10 further comprises driver circuitry 30, 32 and 33, coupled to each of the radiator coils, which drives coils 22, 24 and 26 at the respective driving frequencies $\omega_1$, $\omega_2$ and $\omega_3$. The signals generated by sensor coils 27, 28 and 29 are preferably received and processed by signal processing circuitry 34 and then used by computer 36 to calculate position and orientation coordinates of probe 20.

FIG. 1 shows three radiator coils 22, 24 and 26 and three sensor coils 27, 28 and 29 in a probe 20. It will be understood, however, that the present invention is equally applicable to tracking systems comprising one, two, four or more radiator coils and one, two or more sensor coils. For six-dimensional tracking of probe 20 (three degrees of translation and three degrees of rotation), however, system 10 preferably include a total of six coils, counting both the radiator and sensor coils. Furthermore, although in preferred embodiments of the present invention are described here with reference to frequency-multiplexing of the radiator coils, the principles of the invention may similarly be applied to coils that are time-multiplexed or driven using other methods known in the art to distinguish their respective magnetic fields one from another. The present invention may be used in tracking other types of objects, as well.

In the absence of parasitic effects, the signals generated by sensor coils 27, 28 and 29 at frequency $\omega_1$ are proportional to the amplitude of the time derivative of the projection of field $\vec{H}_1$, at probe 20 along the respective axes of the sensor coils. The signals generated at frequencies $\omega_2$ and $\omega_3$ are similarly proportional to the projections of $\vec{H}_2$ and $\vec{H}_3$. Parasitic effects that may arise due to mutual inductance among the radiator coils are preferably substantially eliminated, as disclosed, for example, in PCT patent application Ser. No. PCT/IL/00100, filed Mar. 18, 1997, which is assigned to the assignee of the present patent application, and whose disclosure is incorporated herein by reference.

Since the direction and amplitude of the magnetic field due to any one of radiator coils 22, 24 and 26 can be calculated easily using methods known in the art, the sensor coil signals due to the respective radiator coil field may be directly related to the sensor coil's distance from and orientation relative to the radiator coil. It will also be appreciated that in the absence of parasitic magnetic fields, such as will be described below, the phases of the signals at frequencies $\omega_1$, $\omega_2$ and $\omega_3$ are substantially constant relative to the phases of the magnetic fields generated by radiator coils 22, 24 and 26, independent of the position and orientation of sensor coils 27, 28 and 29.

As shown in FIG. 1, however, when a metal or magnetic field-responsive article, for example surgical tool 40, is introduced into the vicinity of probe 20, the article will generally receive energy from fields $\vec{H}_1$, $\vec{H}_2$ and $\vec{H}_3$, and re-radiate parasitic magnetic fields, $\vec{H}'_1$, $\vec{H}'_2$ and $\vec{H}'_3$, at frequencies $\omega_1$, $\omega_2$ and $\omega_3$. Generally the phases of the parasitic fields will be shifted relative to the radiator coil fields by phase angles $\phi_1'$, $\phi_2'$ and $\phi_3'$, respectively. The phases and amplitudes of the parasitic fields generally depend on properties of tool 40, including its dielectric constant, magnetic permeability, geometrical shape and orientation relative to the radiator coils. Although the phases may of the parasitic fields may generally vary as a function of the tool's position and orientation, in certain cases the phases will be substantially constant, for example, when tool 40 has suitable symmetry with respect to the fields generated by coils 22, 24 and 26, or when the tool comprises material of negligible resistivity.

The parasitic fields produced by tool 40 will cause corresponding parasitic signal components to be generated in sensor coils 27, 28 and 29, so that the total signal I(t) received from any one of the sensor coils, including both position and parasitic signal components may generally be expressed as:

$$I(t) = \sum_i I_i(t) = \sum_i A_i \sin(\omega_i t + \phi_i) + A'_i \sin(\omega_i t + \phi'_i) \qquad (1)$$

where $A_i, \phi_i, A_i'$ and $\phi_i'$ are the amplitude and phase of the position signal component and the parasitic signal component, respectively, at frequency $\omega_i$.

It will be observed in equation (1) that for each of the signal frequency components Ii, the superposition of the parasitic signal component will cause a phase shift in the total detected signal, relative to the signal phase in the absence of metal tool 40, given by:

$$\phi_i^{total} = \phi_i + \arctan\left[\frac{A_i' \sin\phi_i'}{A_i + A_i' \cos\phi_i'}\right] \quad (2)$$

In preferred embodiments of the present invention, signal processing circuitry 34 and computer 36 detect and record a baseline phase of the signals received from sensor coils 27, 28 and 29 in the absence of any metal or other interfering magnetic field-responsive objects in the vicinity of probe 20. Alternatively, undisturbed phases of the position signal components may have been determined in advance for system 10 or are known based on the operation of the system. When metal tool 40 is introduced into the vicinity of probe 20, the phase shift due to the parasitic components engendered thereby in the signals is detected, and computer 36 may present a message to an operator of the probe, indicating that the determination of the probe's position may be inaccurate. Preferably, the amplitudes $A_i'$ of the parasitic signal components are measured, for example as described below, and are then used to estimate and inform the operator of an error bound on the position coordinates determined by computer 36.

Generally, the baseline phase of the signals received from sensor coils 27, 28 and 29 will be substantially constant, in the absence of interfering objects such as tool 40. If circuitry 34 receives a signal having a variable phase, particularly a randomly variable phase, such a signal is typically indicative of a malfunction in system 10, for example, a loose connection between one of the sensor coils and the circuitry. In such a case, probe 20 should be removed and repaired.

Figure 2:
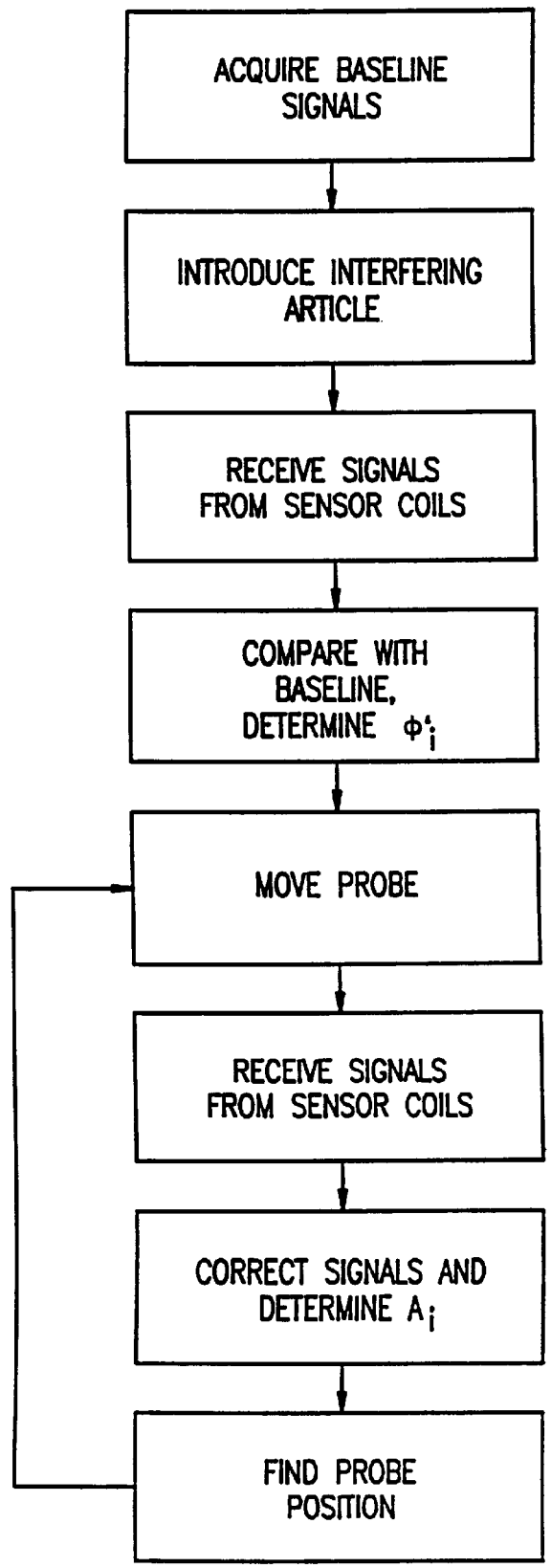
FIG. 2 is a flow chart illustrating a method for tracking an object, in accordance with a preferred embodiment of the present invention.

FIG. 2 illustrates schematically a method for detecting interference due to tool 40 or due to another magnetic field-responsive article, and determining the correct position of probe 20 in the presence of such interference, in accordance with preferred embodiments of the present invention. Preferably, normalized baseline signals are first acquired by computer 36 at each of frequencies $\omega_i$ in the absence of tool 40 or any other interfering article. Subsequently, after the tool is introduced into the vicinity of the probe 20, these baseline signals are compared with signals received from sensor coils 27, 28 and 29, using methods of signal correlation known in the art, for example, in order to measure the phase shifts $\phi_i'$. Preferably, the phase shifts are measured for different positions and orientations of the tool, in order to ascertain the extent to which the phase shifts $\phi_i'$ vary with tool position and orientation. If the measured phase shifts are found to be generally constant (or are known to be so from previous measurement), they may be used to calculate corrected values of $A_i$, for example, based on formula (1). The position of probe 20 is then found with sufficient accuracy even in the presence of parasitic magnetic fields due to tool 40.

Preferably, in order to measure phase shifts $\phi'_i$, probe 20 is held immobile while tool 40 is being moved into its vicinity. Any changes in the amplitudes and phases of the signals received from sensor coils 27, 28 and 29 are then known to be associated with distortions of the magnetic field due to the article. These changes are detected and used in measuring the effect of the distortions on the determination of the probe's position coordinates.

Specifically, the detected changes may be used to measure the phase shifts $\phi'_i$ of the parasitic fields, relative to the radiator coil fields. At low RF frequencies, for example up to 10 kHz, if tool 40 is sufficiently symmetrical and/or comprises material of negligible resistivity, the phase shifts $\phi'_i$ of the re-radiated fields will not change significantly as the tool is moved. Therefore, one measurement of $\phi'_i$, made while probe 20 is held in any desired position and tool 40 is in any other suitable position in a vicinity of the probe, may be sufficient for calculating values of $A_i$ that are substantially corrected for the effect of the re-radiated fields, at all other positions of interest of probe 20 and tool 40.

In the above preferred embodiment of the present invention, it is assumed that the re-radiated fields are the dominant source of magnetic field distortion due to tool 40. Distortion of the lines of magnetic field due to the magnetic permeability of tool 40 gives rise to parasitic magnetic field components that are generally in phase with fields $\vec{H}_1$, $\vec{H}_2$ and $\vec{H}_3$, and are therefore more difficult to quantify and correct for.

Figure 3:
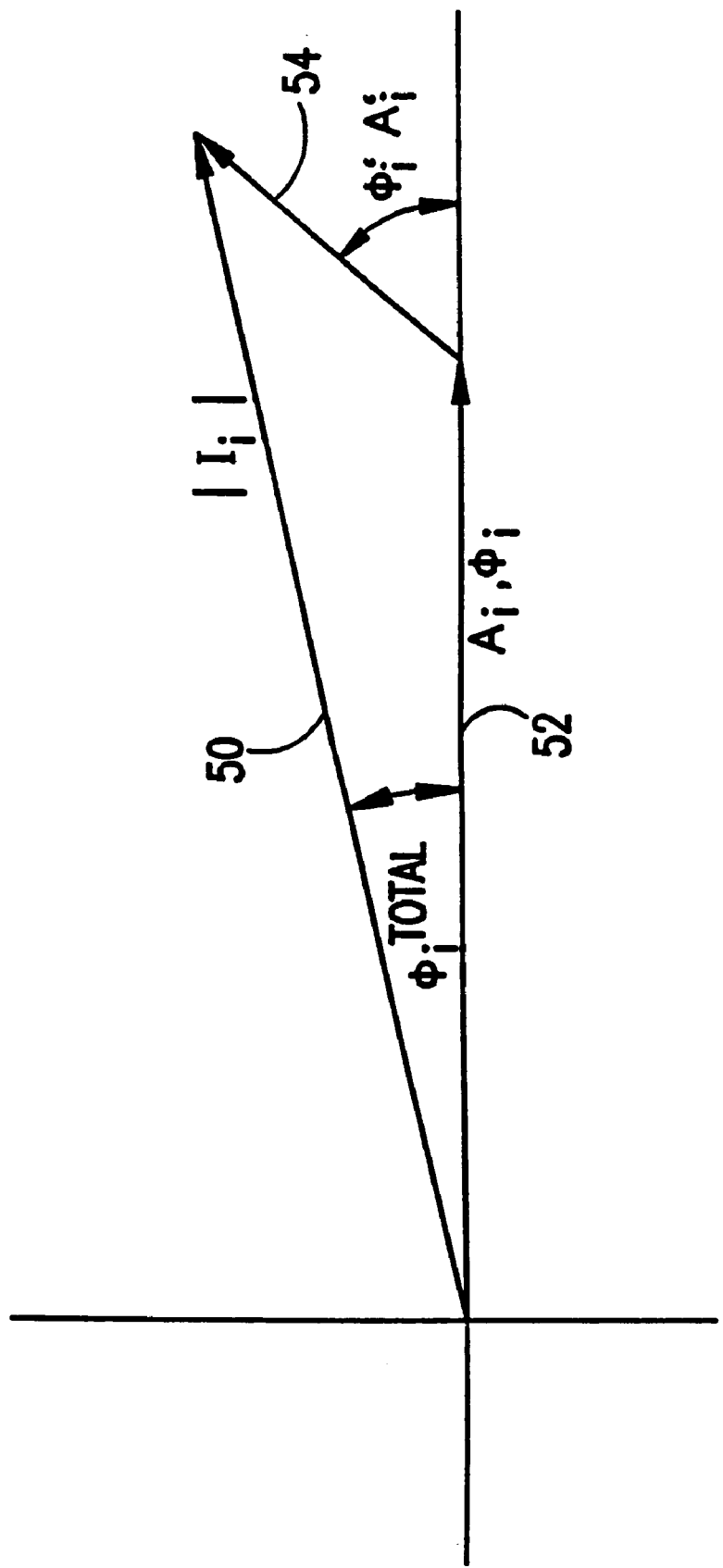
FIG. 3 is a vector diagram useful in understanding principles of the present invention.

FIG. 3 is a vector diagram illustrating the method described above for separating the position and parasitic signal components. Signal vector 50, having amplitude $|I_i|$ and phase $\phi_i$ total, represents the signal received from one of the sensor coils at frequency $\omega_i$. Vector 50 is the vector sum of position signal component vector 52 and parasitic signal component vector 54. Position signal component 52 has amplitude $A_i$ and known, substantially constant phase $\phi_i$, which is arbitrarily assigned the value zero, without loss of generality. If the phase $\phi_i'$ (for the cases described above, in which $\phi_i'$ can be considered to be substantially constant) of parasitic signal component 54 is also known, for example having been measured as described above, then a triangle defined by vectors 50, 52 and 54 is completely determined, since all its angles ($\phi_i$, $\phi_i'$ and $\phi_i$ total) and one of its sides ($|I_i|$) are known. Respective amplitudes $A_i$ and $A_i'$ are thus uniquely determined, and the coordinates of probe 20 may be found accurately based on the values of $A_i$ determined from the trigonometric formula:

$$A_i = |I_i|\frac{\sin(\phi_i' - \phi_i^{total})}{\sin(\phi_i')} \quad (3)$$

The method illustrated by FIG. 3 assumes that the phases of the parasitic signal components are shifted relative to the position signal components. However, when tool 40 or another magnetic field-responsive article in the vicinity of probe 20 has magnetic permeability, $\mu$, that is significantly different from that of air, the lines of magnetic field may be substantially distorted, without significant phase shift. In this case, changes in the amplitudes of the signals from sensor coils 27, 28 and 29 are preferably detected as tool 40 is being introduced into the vicinity of probe 20, and are used to estimate an error bound on the position coordinates calculated by computer 36 in the presence of the tool. Generally the error will be greatest when probe 20 is closely adjacent to tool 40, and decrease as the distance between them increases.

It will be understood that while the above methods have been described with reference to a system comprising three radiator coils and three sensor coils, they may equally be applied to other electromagnetic object tracking system, using greater or fewer numbers of coils or antennae.

It will further be understood that the principles of the present invention may similarly be applied to object tracking systems based on other types of RF electromagnetic fields, wherein a sensor associated with the object generates signals whose amplitude and phase are dependent on the amplitude and phase of the radiation fields.

Moreover, it will be appreciated that the preferred embodiments described above are cited by way of example, and the full scope of the invention is limited only by the claims.

What is claimed is:

1. A method for tracking an object using an energy field, in the presence of interference due to introduction of an article responsive to the field, in the vicinity of the object, comprising:

producing a first energy field in the vicinity of the object;

identifying and determining a characteristic of a parasitic energy field induced responsive to the first field, due to introduction of the article;

receiving signals responsive to the first energy field and the parasitic energy field generated at a plurality of locations of the object after introduction of the article; and determining spatial coordinates of the object responsive to the generated signals and the determined characteristic by determining a phase shift of the signals responsive to the parasitic energy field with respect to the signals responsive to the first energy field.

2. A method in accordance with claim 1, wherein determining spatial coordinates comprises:

determining an amplitude of the signals generated at a location of the object;

processing the amplitude to find a corrected amplitude using the determined characteristic; and calculating the coordinates based on the corrected amplitude.

3. A method in accordance with claim 2, wherein determining the characteristic of the induced energy fields comprises:

receiving a first signal responsive to the energy field in the absence of the field-responsive article;

introducing the article into the vicinity of the object;

receiving a second signal responsive to the energy field in the presence of the article; and processing the first and second signals to determine the characteristic.

4. A method in accordance with claim 3, wherein processing the first and second signals comprises:

finding a first amplitude A and a first phase $\phi$ of the first signal;

finding a second amplitude and a second phase $\phi^{total}$ of the second signal; and determining a phase shift $\phi'$, associated with the induced field, based on the first and second amplitudes and the first and second phases.

5. A method in accordance with claim 4, wherein determining the phase shift $\phi'$ comprises finding values of $\phi'$ and of a third amplitude A' associated with the induced field, substantially as given by:

$$\phi^{total} = \phi + \arctan\left[\frac{A'\sin\phi'}{A + A'\cos\phi'}\right].$$

6. A method in accordance with claim 5, wherein determining spatial coordinates comprises:

measuring an uncorrected amplitude I and an uncorrected phase $\phi_{un}$ of the signals received at one of the plurality of locations of the object;

finding a corrected amplitude $A_{cor}$, using the phase shift $\phi'$; and calculating the coordinates based on the corrected amplitude.

7. A method in accordance with claim 6, wherein the corrected amplitude is substantially as given by:

$$A_{cor} = |I|\frac{\sin(\phi' - \phi_{un})}{\sin(\phi')}.$$

8. A method in accordance with claim 7, and comprising detecting a malfunction in a system for tracking the object by finding a variability in one or more of the first and second phases.

9. A method in accordance with claim 8, wherein the characteristic is not determined from measurements made at the location.

10. A method in accordance with claim 1, and comprising detecting the second energy field and notifying a user that the article has been introduced.

11. A method in accordance with claim 10, wherein determining the spatial coordinates of the object comprises estimating an error bound on the coordinates in the presence of the article.

12. A method in accordance with claim 11, wherein producing the energy fields comprises producing magnetic fields.

13. A method in accordance with claim 12, wherein receiving the signals comprises receiving electrical signals which are generated responsive to the magnetic field.

14. An object tracking system, comprising:

a radiator, which generates an energy field in the vicinity of the object;

a sensor, fixed to the object, which generates signals responsive to the energy field; and signal processing circuitry, which receives the signals from the sensor and determines position coordinates of the object responsive thereto, while detecting interference in the signals due to introduction into the vicinity of the object of an article responsive to the energy field wherein the circuitry detects a phase shift in the signals due to the introduction of the article.

15. A system according to claim 14, wherein based on the detected phase shift, the circuitry corrects the position coordinates for errors induced due to the interference.

16. A system according to claim 15, wherein the circuitry detects a malfunction in the system by finding a variability in the phase shift.

17. A system according to claim 16, wherein the circuitry notifies a user of the system that the article has been introduced, based on the detected interference.

18. A system according to claim 17, wherein the circuitry determines an error bound on the coordinates, based on the detected interference.

19. A system according to claim 18, wherein the energy field comprises a magnetic field, and wherein the signals comprise electrical currents generated responsive to the magnetic field.

* * * * *